(12) United States Patent
Motoki

(10) Patent No.: US 8,821,379 B2
(45) Date of Patent: Sep. 2, 2014

(54) INDUSTRIAL ENDOSCOPE APPARATUS

(75) Inventor: Ryoji Motoki, Yokohama (JP)

(73) Assignee: Olympus Corporation, Tokyo (JP)

(*) Notice: Subject to any disclaimer, the term of this patent is extended or adjusted under 35 U.S.C. 154(b) by 126 days.

(21) Appl. No.: 13/528,313

(22) Filed: Jun. 20, 2012

(65) Prior Publication Data
US 2013/0079594 A1 Mar. 28, 2013

(30) Foreign Application Priority Data

Sep. 22, 2011 (JP) ................................ P2011-208012

(51) Int. Cl.
*A61B 1/04* (2006.01)
*A61B 1/00* (2006.01)
*G02B 23/24* (2006.01)

(52) U.S. Cl.
CPC ........ *A61B 1/00039* (2013.01); *G02B 23/2484* (2013.01); *A61B 1/00052* (2013.01); *A61B 1/0005* (2013.01)
USPC ............................ 600/109; 600/117; 600/137

(58) Field of Classification Search
CPC .... A61B 19/56; A61B 19/5244; A61B 1/045; A61B 1/00009; A61B 1/00045; A61B 1/00048; A61B 1/0005; A61B 1/00052; A61B 1/00055
USPC .......... 600/103, 117, 137, 139, 145–152, 160
See application file for complete search history.

(56) References Cited

U.S. PATENT DOCUMENTS

| | | | |
|---|---|---|---|
| 5,099,850 A * | 3/1992 | Matsui et al. ................. | 600/463 |
| 5,836,869 A * | 11/1998 | Kudo et al. .................... | 600/173 |
| 7,435,216 B2 * | 10/2008 | Kwon et al. ................... | 600/139 |
| 7,641,609 B2 * | 1/2010 | Ohnishi et al. ................. | 600/117 |
| 7,659,912 B2 * | 2/2010 | Akimoto et al. ............... | 345/619 |
| 7,660,623 B2 * | 2/2010 | Hunter et al. .................. | 600/424 |
| 8,211,008 B2 * | 7/2012 | Henzler ......................... | 600/109 |
| 8,602,967 B2 * | 12/2013 | Robertson ...................... | 600/103 |
| 2002/0161280 A1 * | 10/2002 | Chatenever et al. ........... | 600/112 |
| 2002/0183592 A1 * | 12/2002 | Suzuki et al. .................. | 600/145 |
| 2003/0078475 A1 * | 4/2003 | Hirata et al. ................... | 600/152 |
| 2003/0114730 A1 * | 6/2003 | Hale et al. ...................... | 600/114 |
| 2005/0228230 A1 * | 10/2005 | Schara et al. .................. | 600/171 |
| 2005/0272971 A1 * | 12/2005 | Ohnishi et al. ................. | 600/101 |
| 2006/0015012 A1 * | 1/2006 | Sato .............................. | 600/118 |

(Continued)

FOREIGN PATENT DOCUMENTS

JP 2009-089955 A 4/2009

*Primary Examiner* — Anhtuan T Nguyen
*Assistant Examiner* — William Chou
(74) *Attorney, Agent, or Firm* — Holtz Holtz Goodman & Chick PC

(57) ABSTRACT

This endoscope apparatus includes: an insertion portion configured to include a bend portion; an image pickup portion configured to capture an image of an object to be inspected; an operation portion configured to perform a bending operation of the bend portion; a storage portion configured to store at least an image of the objected to be inspected as a recorded image; a display portion configured to display the image, and a display control portion configured to: determine a display orientation of a superimposition information; display the image captured by the image pickup portion without rotating the image; and display the superimposition information, the display control portion being further configured to: determine a display orientation of at least one of the recorded image and a Graphical User Interface; and display the at least one of the recorded image and the Graphical User Interface.

13 Claims, 11 Drawing Sheets

(56) References Cited

U.S. PATENT DOCUMENTS

| | | | |
|---|---|---|---|
| 2006/0036125 A1* | 2/2006 | Viswanathan et al. | 600/11 |
| 2006/0041178 A1* | 2/2006 | Viswanathan et al. | 600/11 |
| 2006/0041180 A1* | 2/2006 | Viswanathan et al. | 600/11 |
| 2006/0084840 A1* | 4/2006 | Hoeg et al. | 600/117 |
| 2007/0173694 A1* | 7/2007 | Tsuji et al. | 600/146 |
| 2008/0159653 A1* | 7/2008 | Dunki-Jacobs et al. | 382/293 |
| 2012/0078043 A1* | 3/2012 | Miyayashiki et al. | 600/109 |
| 2013/0172906 A1* | 7/2013 | Olson et al. | 606/130 |

\* cited by examiner

INDUSTRIAL ENDOSCOPE APPARATUS

BACKGROUND OF THE INVENTION

1. Field of the Invention

The present invention relates to an endoscope apparatus, and a method of displaying images. Priority is claimed on Japanese Patent Application No. 2011-208012, filed on Sep. 22, 2011, the content of which is incorporated herein by reference.

2. Description of Related Art

Conventionally, industrial endoscope apparatuses are known (for example, see Japanese Unexamined Patent Application, First Publication No. 2009-089955). There are known endoscope apparatuses provided with an image rotation function capable of rotating and displaying an endoscopic image and an OSD (on-screen display) on the display portion for ease of inspection even if the endoscope apparatuses are used in the inverted orientation. In addition, endoscope apparatuses are known in which the operation portion and the display portion are arranged in the same housing (all-in-one endoscope apparatuses).

SUMMARY OF THE INVENTION

According to an aspect of the present invention, an endoscope apparatus includes: an insertion portion configured to include a bend portion; an image pickup portion configured to capture an image of an object to be inspected; an operation portion configured to perform a bending operation of the bend portion; a storage portion configured to store at least an image of the objected to be inspected as a recorded image; a display portion configured to display the image, the display portion having a fixed positional relationship relative to the operation portion; and a display control portion configured to: determine a display orientation of a superimposition information, the superimposition information being superimposed on the image; display the image captured by the image pickup portion without rotating the image; and display the superimposition information according to the display orientation of the superimposition information, the display control portion being further configured to: determine a display orientation of at least one of the recorded image and a Graphical User Interface; and display the at least one of the recorded image and the Graphical User Interface according to the display orientation of the at least one of the recorded image and the Graphical User Interface.

DETAILED DESCRIPTION OF THE INVENTION

Figure 1:
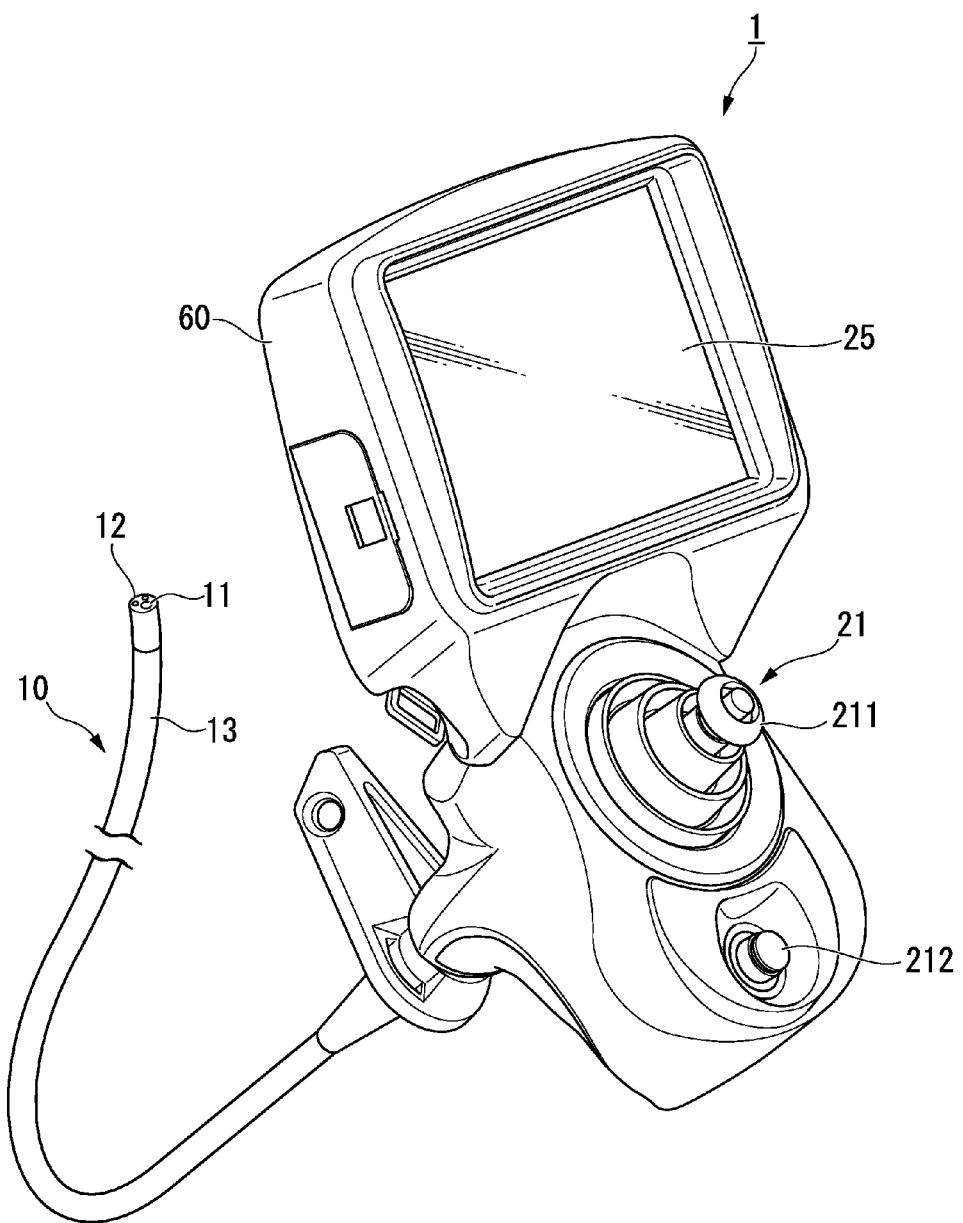
FIG. 1 is an overall perspective view showing an appearance of an endoscope apparatus according to one embodiment of the present invention.

Hereunder is a description of one embodiment of the present invention with reference to the drawings. FIG. 1 is an overall perspective view showing an appearance of an endoscope apparatus in the present embodiment. The endoscope apparatus 1 of the present embodiment is used for observing an inspection target located at the end of an elongated insertion channel, an internal portion of the inspection target, and the like. In the exemplary illustration, the endoscope apparatus 1 includes: an insertion portion 10; an operation portion 21 for performing a bending operation of the insertion portion 10; a display portion 25 for displaying a video picture obtained by the insertion portion 10; and a housing portion 60 for containing the operation portion 21 and the display portion 25.

Figure 2:
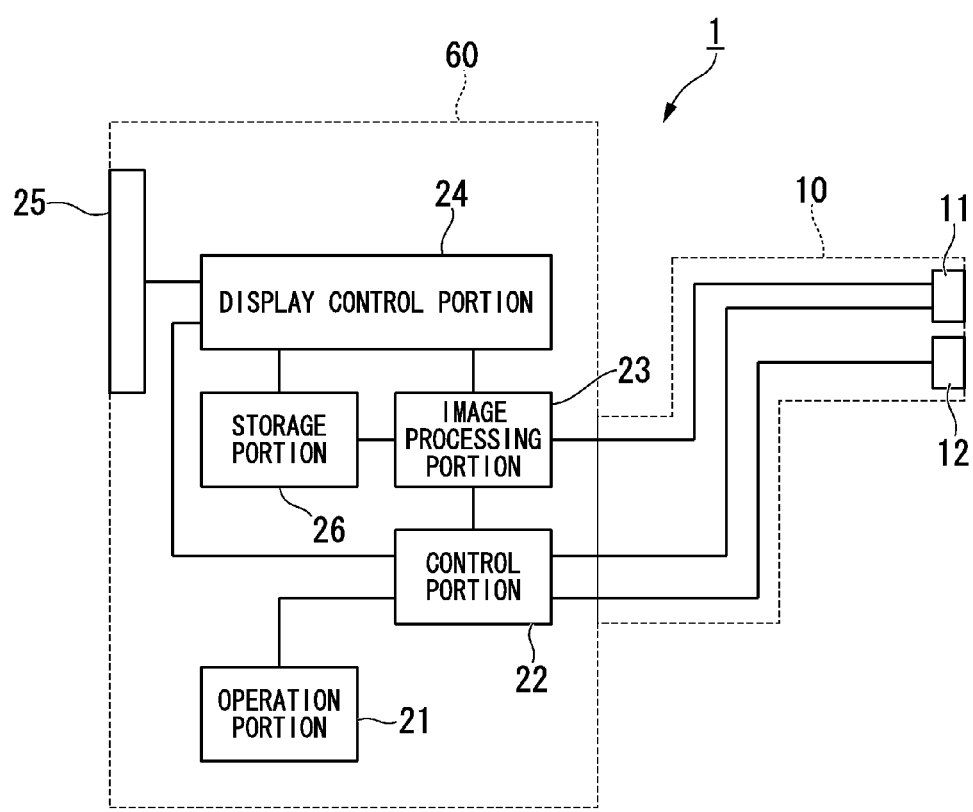
FIG. 2 is a block diagram showing a configuration of the endoscope apparatus of the embodiment.

FIG. 2 is a block diagram showing a configuration of the endoscope apparatus 1 of the present embodiment. The housing portion 60 of the endoscope apparatus 1 includes an operation portion 21; a control portion 22; an image processing portion 23; a display control portion 24; a display portion 25; and a storage portion 26.

The image pickup portion 11, the illumination portion 12, and the operation portion 21 are constructed as described above. The control portion 22 controls the constituent elements included in the endoscope apparatus 1. The image processing portion 23 performs image processing on an image captured by the image pickup portion 11. The display control portion 24 controls the display portion 25, and causes the display portion 25 to display an image of an inspection target. The display portion 25 includes a display such as a LCD (Liquid Crystal Display), and displays an image through control by the display control portion 24. The storage portion 26 stores: the images captured by the image pickup portion 11; and the information necessary to the operations of the constituent elements included in the endoscope apparatus 1.

In the exemplary illustration shown in FIG.1, the endoscope apparatus 1 is oriented so that the display portion 25 is above the operation portion 21. When the user operates the endoscope apparatus 1 in this position, it is defined that the user operates the endoscope apparatus 1 in a correctly directed position [C]. In this case, the control portion 22 generates a signal indicating that a position of the endoscope apparatus 1 is the correctly directed position.

The insertion portion 10 includes an image pickup portion 11 and an illumination portion 12 at its distal end. The image pickup portion 11 includes an image pickup element such as a CCD (Charge Coupled Device). The image pickup portion 11 is capable of obtaining an image such as a still image and/or a streaming image of an inspection target or the like ahead of the distal end portion. The illumination portion 12 includes an LED (Light Emitting Diode) or the like. The illumination portion 12 emits light ahead of the distal end portion. The insertion portion 10 further includes a bend portion 13 in which a plurality of knot rings or bender pieces (not shown in the figure and hereinafter referred to generically as "knot rings or the like") are aligned in the axis line direction of the insertion portion 10 and connected to each other. The insertion portion 10 is capable of bending in four directions in two axes that cross its central axis line, so as to be spaced away from the central axis line. Four operation members such as wires corresponding to the aforementioned four directions are connected to the knot ring or the like closest to the distal end out of all the knot rings or the like. The operation members extend through the knot rings or the like to the inside of the housing portion 60, and are connected to the operation portion 21 there.

The operation portion 21 includes: a first joy stick 211 for operating the bend portion 13; a second joy stick 212 for operating a cursor or the like that is displayed on the display portion 25; and a bending mechanism that is operated via the first joy stick 211. The operation portion 21 (the first joy stick 211) of the present embodiment employs a mechanical mechanism in which the bend portion 13 is bent by pulling the operation members through an inclining operation. However, the operation portion 21 (the first joy stick 211) may employ an electrical mechanism of pulling the operation members by use of a drive device such as a motor in accordance with electrically-detected inclination amount and inclination direction, to thereby operate the bend portion 13.

Figure 3:
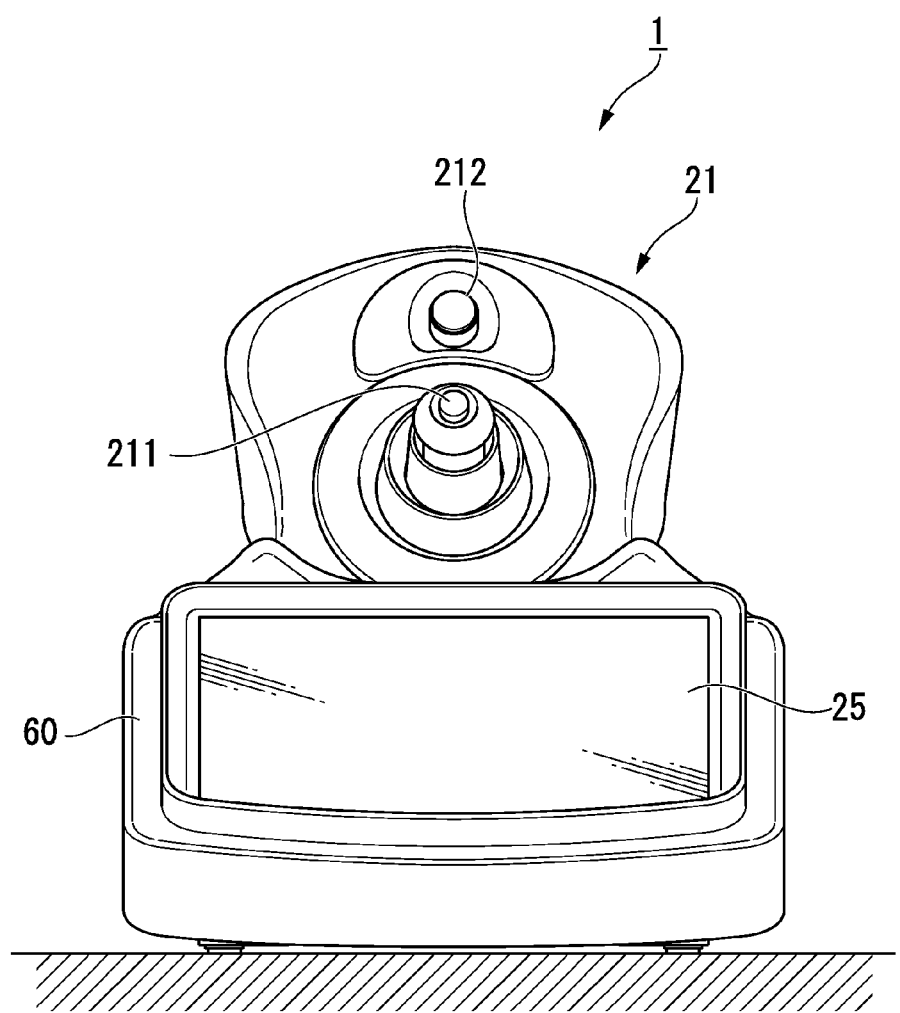
FIG. 3 is a front view showing the appearance of the endoscope apparatus of the embodiment when the orientation of the endoscope apparatus is inverted.
Figure 4:
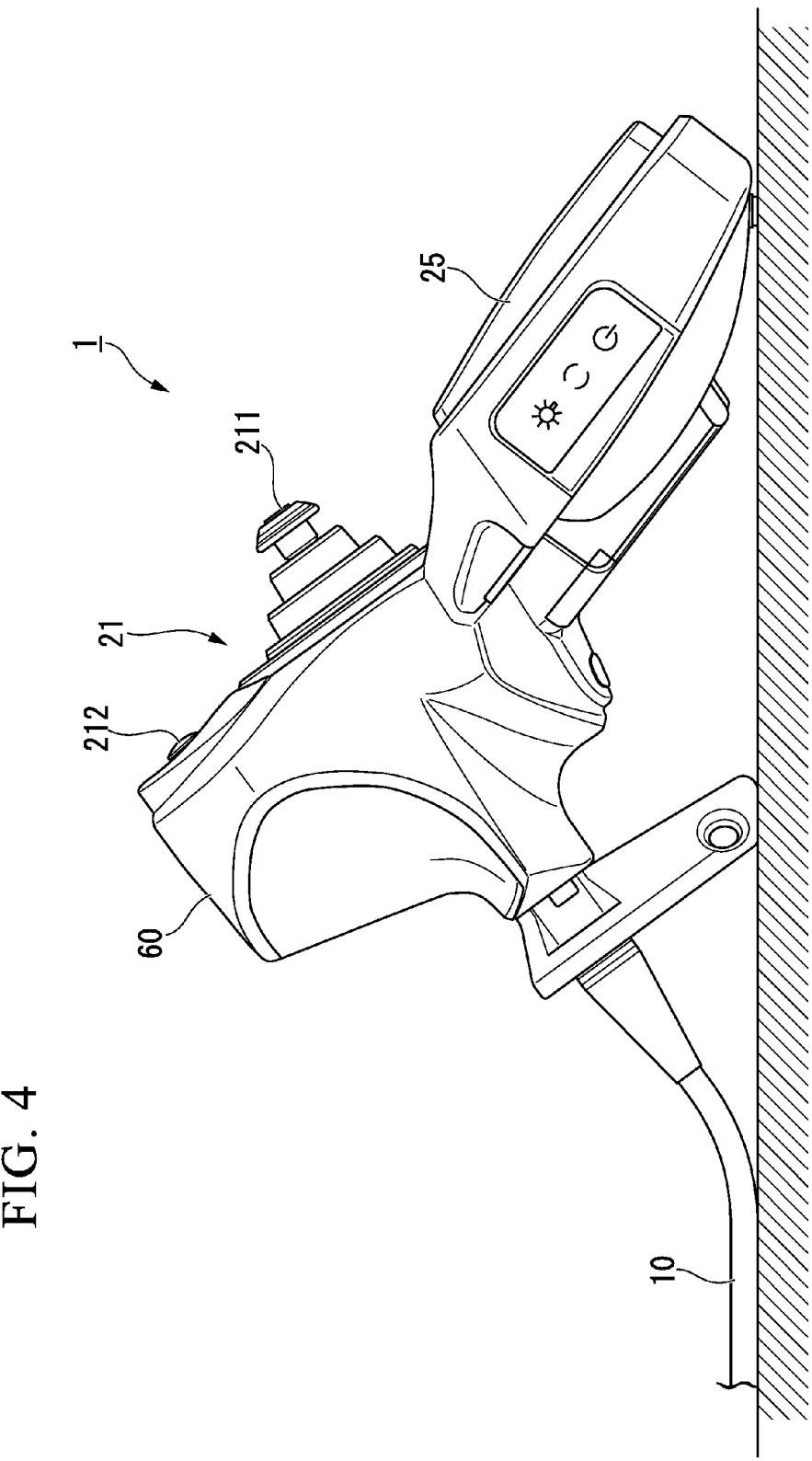
FIG. 4 is a side view showing the appearance of the endoscope apparatus of the embodiment when the orientation of the endoscope apparatus is inverted.

Next is a description of a relationship between the operation portion 21 and the display portion 25 when the endoscope apparatus 1 is inverted. FIG. 3 is a front view showing an appearance of the endoscope apparatus 1 of the present embodiment when the endoscope apparatus 1 is inverted (when the display portion 25 is placed upside down). FIG. 4 is a side view showing the appearance of the endoscope apparatus 1 when the endoscope apparatus 1 of the present embodiment is inverted. In the exemplary illustration, the endoscope apparatus 1 has the display portion 25 placed upside down, and hence, in the position where the operation portion 21 is above the display portion 25. When the user operates the endoscope apparatus 1 in this position, it is defined that the user operates the endoscope apparatus 1 in an oppositely directed position. In this case, the control portion 22 generates a signal indicating that a position of the endoscope apparatus 1 is the oppositely directed position.

Figure 5A:
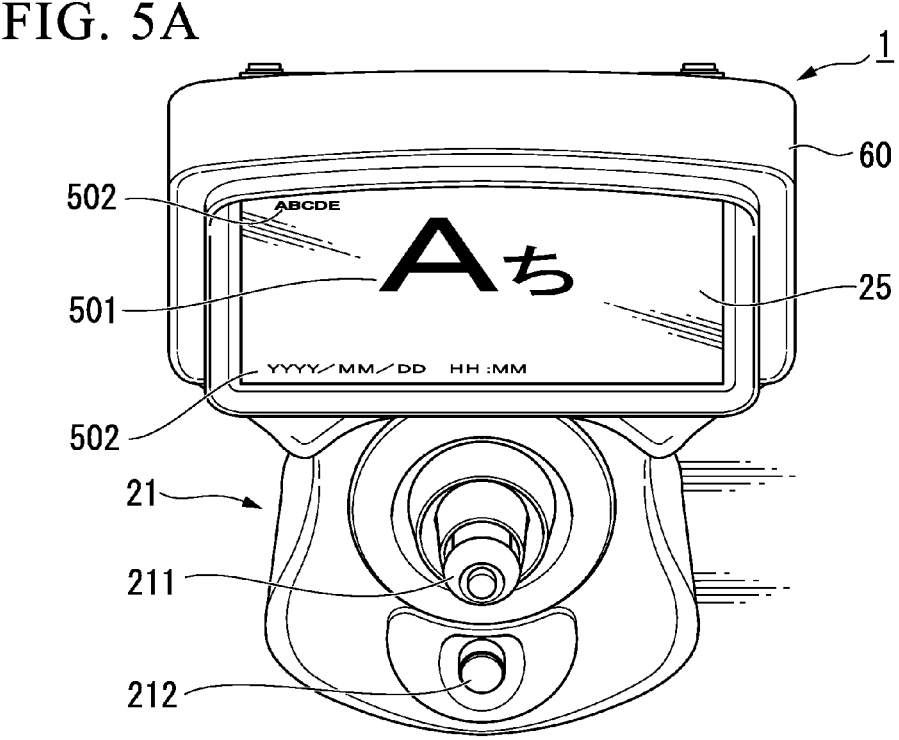
FIG. 5A is a schematic diagram showing an example where a display control portion displays, on a display portion, an image captured by an image pickup portion and OSDs in a non-rotated state in the embodiment.
Figure 5B:
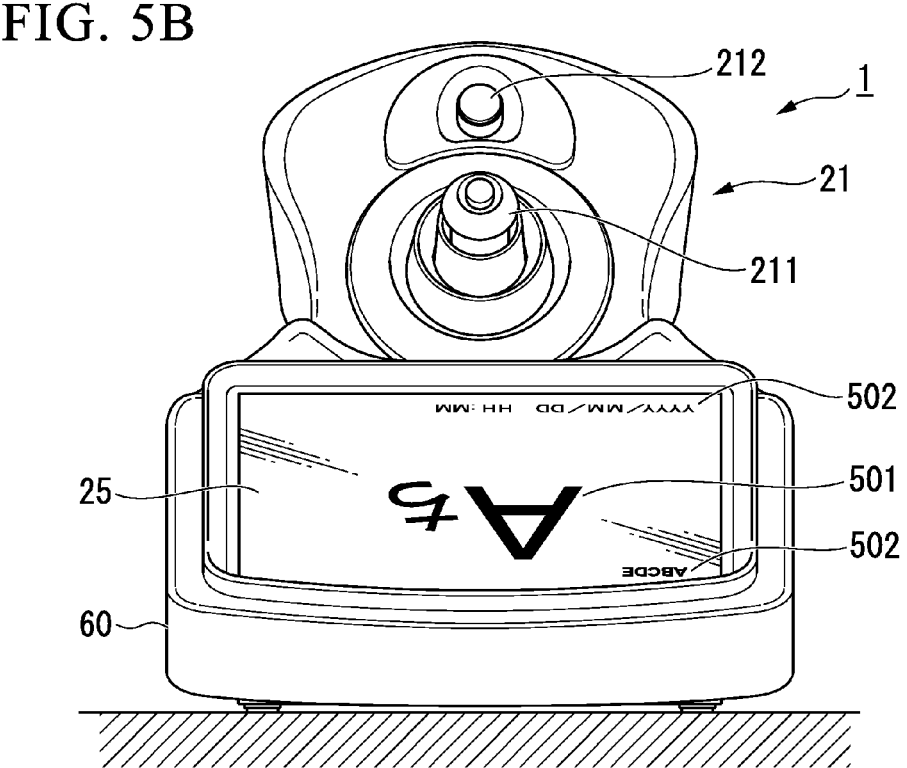
FIG. 5B is a schematic diagram showing an example where the display control portion displays, on the display portion, the image captured by an image pickup portion and the OSDs in the non-rotated state in the embodiment.
Figure 6A:
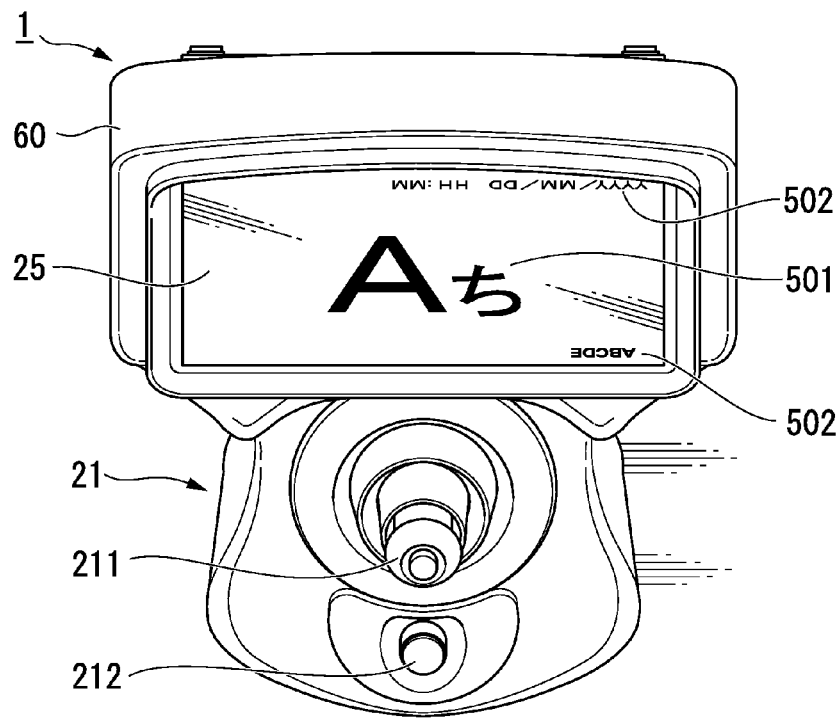
FIG. 6A is a schematic diagram showing an example where the display control portion displays, on the display portion, the image captured by an image pickup portion in the non-rotated state, and the OSDs in an rotated state.
Figure 6B:
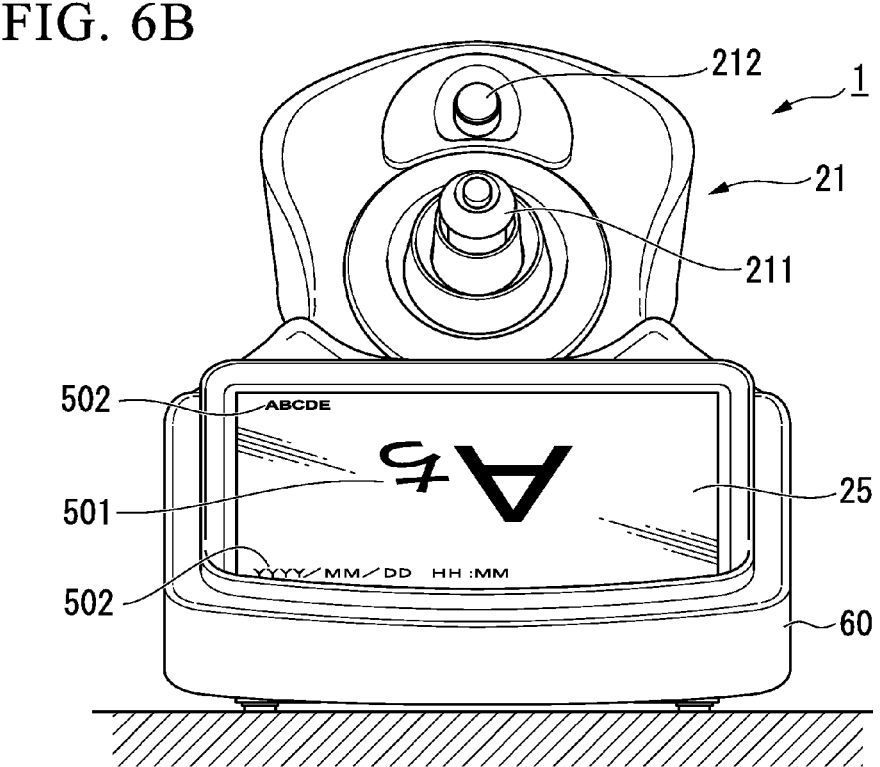
FIG. 6B is a schematic diagram showing an example where the display control portion displays, on the display portion, the image captured by the image pickup portion in the non-rotated state, and the OSDs in the rotated state.

Next is a description of an example where the display control portion 24 causes the display portion 25 to display an image when the image pickup portion 11 is capturing an image (a streaming image and/or a still image). FIG. 5A and FIG. 5B are schematic diagram showing an example where the display control portion 24 causes the display portion 25 to display an image captured by the image pickup portion 11 and to display an OSD (On-Screen Display) in a non-rotated state (a state displaying an image, an OSD, or the like without being rotated). FIG. 6A and FIG. 6B are schematic diagrams showing an example where the display control portion 24 causes the display portion 25 to display the image captured by the image pickup portion 11 in the non-rotated state and to display the OSD in a rotated state (approximately turned 180 degrees). The image captured by the image pickup portion 11 includes a streaming image and/or a still image. A streaming image is a realtime image being captured by the image pickup portion 11. A still image is a paused image of a streaming image. An OSD includes date, time, and/or additional information (superimposition information) that are superimposed on the image displayed on the display portion 25.

FIG. 5A is a schematic diagram of an example where the display control portion 24 causes the display portion 25 to display the image captured by the image pickup portion 11 and to display the OSD when the user is operating the endoscope apparatus 1 in the correctly directed position. As is illustrated, the user operates the endoscope apparatus 1 in the correctly directed position, and the display control portion 24 causes the display portion 25 to display an image 501 captured by the image pickup portion 11 and to display OSDs 502 in the non-rotated state. In this case, the direction of the operation on the operation portion 21 by the user coincides with the direction in which the image 501 displayed on the screen moves by the bend portion 13 being bent. Furthermore, in this case, the user can read the letters on the OSDs 502 in the non-rotated state. Accordingly, the user is capable of easily performing a bending operation of the bend portion 13.

FIG. 5B is a schematic diagram showing an example where the display control portion 24 causes the display portion 25 to display the image captured by the image pickup portion 11 and to display the OSD in the non-rotated state when the user is operating the endoscope apparatus 1 in the oppositely directed position. As is illustrated, the user operates the endoscope apparatus 1 in the oppositely directed position, and the display control portion 24 causes the display portion 25 to display an image 501 captured by the image pickup portion 11 and to display OSDs 502 in the non-rotated state. In this case, the direction of the operation on the operation portion 21 by the user coincides with the direction in which the image 501 displayed on the screen moves by the bend portion 13 being bent. However, the letters on the OSDs 502 look rotated at 180 degrees for the user.

Therefore, there is a possibility that the use is not capable of easily checking the OSDs 502. If both of the image 501 and the OSDs 502 are displayed in the rotated state in this case, the direction of the operation on the operation portion 21 by the user is opposite to the direction in which the image 501 displayed on the screen moves by the bend portion 13 being bent.

FIG. 6A and FIG. 6B are diagrams showing an example where the display control portion 24 causes the display portion 25 to display the image captured by the image pickup portion 11 in the non-rotated state and to display the OSDs in the rotated state (substantially turned 180 degrees). The exemplary illustrations in FIG. 6A and FIG. 6B show the case where the user is capable of easily checking the OSD and also of easily performing an bending operation of the bend portion 13 when operating the endoscope apparatus 1 in the correctly directed position. The detailed description is as follows. FIG. 6A is a schematic diagram showing an example where the display control portion 24 causes the display portion 25 to display the image 501 captured by the image pickup portion 11 in the non-rotated state and to display the OSDs 502 in the rotated state when the user is operating the endoscope apparatus 1 in the correctly directed position. As is illustrated, the user operates the endoscope apparatus 1 in the correctly directed position, and the display control portion 24 causes the display portion 25 to display the image 501 captured by the image pickup portion 11 in the non-rotated state and to display the OSDs 502 in the rotated state. In this case, the direction of the operation on the operation portion 21 by the user coincides with the direction in which the image 501 displayed on the screen moves by the bend portion 13 being bent. However, the letters on the OSDs 502 look rotated at 180 degrees for the user. Therefore, there is a possibility that the use is not capable of easily checking the OSDs 502.

FIG. 6B is a schematic diagram of an example where the display control portion 24 causes the display portion 25 to display the image captured by the image pickup portion 11 in the non-rotated state and to display the OSDs in the rotated state when the user is operating the endoscope apparatus 1 in the oppositely directed position. As is illustrated, the user operates the endoscope apparatus 1 in the oppositely directed position, and the display control portion 24 causes the display portion 25 to display the image 501 captured by the image pickup portion 11 in the non-rotated state and to display the OSDs 502 in the rotated state. In this case, the direction of the operation on the operation portion 21 by the user coincides with the direction in which the image 501 displayed on the screen moves by the bend portion 13 being bent. Furthermore, the user is capable of looking at the letters on the OSDs 502 even if the user operates the endoscope apparatus 1 in the oppositely directed position. As a result, the direction of the operation on the operation portion 21 by the user is not opposite to the direction in which the image 501 displayed on the screen moves. Therefore, the user is capable of easily checking the OSDs 502 and is also capable of easily performing a bending operation of the bend portion 13.

When the user is operating the endoscope apparatus 1 in the correctly directed position as shown in FIG. 5A, the display control portion 24 causes the display portion 25 to display the image 501 captured by the image pickup portion 11 and to display the OSDs 502 in the non-rotated state. In this case, the user easily checks the OSDs 502 and also performs an bending operation of the bend portion 13. When the user is operating the endoscope apparatus 1 in the oppositely directed position as shown in FIG. 6B, the display control portion 24 causes the display portion 25 to display the image 501 captured by the image pickup portion 11 in the non-rotated state and to display the OSDs 502 in the rotated state. Therefore, the user easily checks the OSDs 502 and performs a bending operation of the bend portion 13.

Therefore, in the present embodiment, the display control portion 24 causes the display portion 25 to display the image captured by the image pickup portion 11 and to display the OSDs in the non-rotated state in a normal mode in which the user uses the endoscope apparatus 1 in the correctly directed position. Additionally, the display control portion 24 causes the display portion 25 to display the image captured by the image pickup portion 11 in the non-rotated state and to display the OSDs in the rotated state in a rotated display mode in which user uses the endoscope apparatus 1 in the oppositely directed position (the position where the display portion 25 is placed upside down).

Figure 7A:
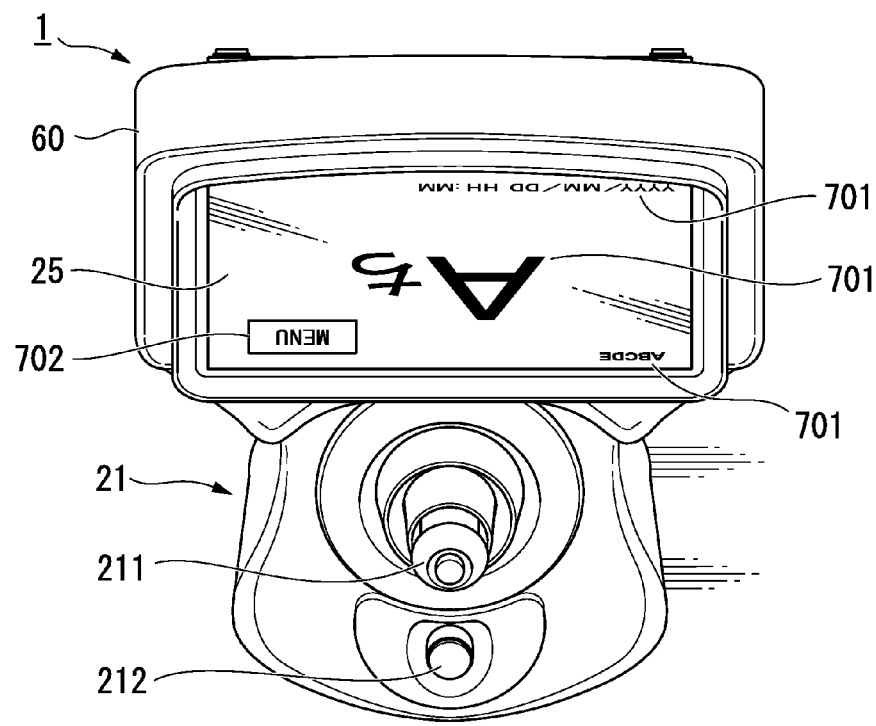
FIG. 7A is a schematic diagram showing an example where the display control portion displays, on the display portion, a recorded image stored by a storage portion and GUI such as a menu screen in the rotated state in the embodiment.
Figure 7B:
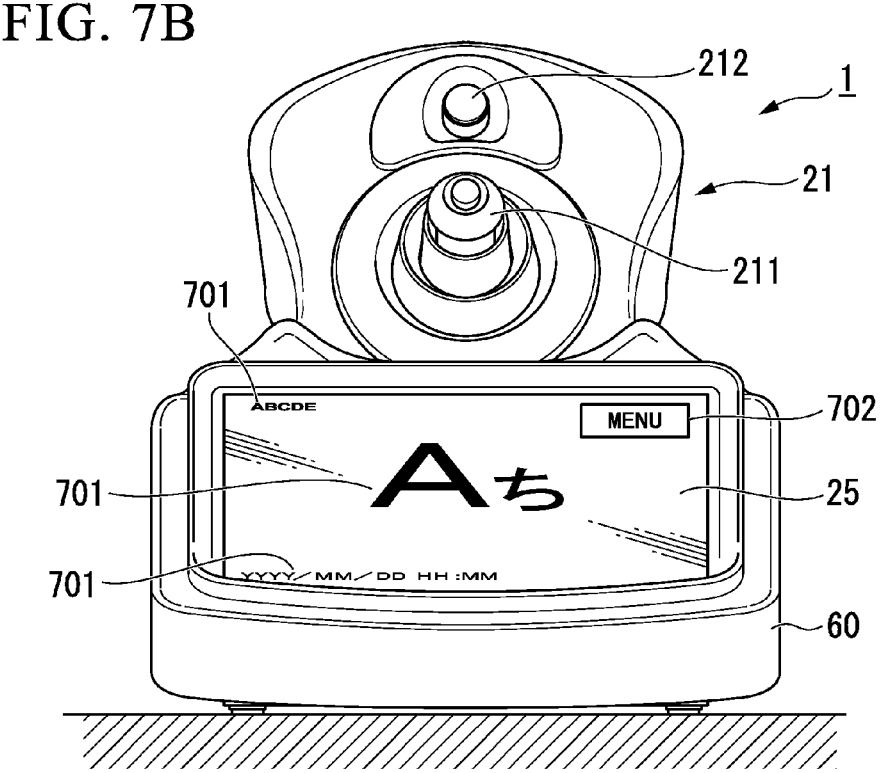
FIG. 7B is a schematic diagram showing an example where the display control portion displays, on the display portion, the recorded image stored by the storage portion and the GUI such as a menu screen in the rotated state in the embodiment.

Next is a description of an example where the display control portion 24 causes the display portion 25 to display a recorded image when the recorded image that has been captured by the image pickup portion 11 and that has been stored by the storage portion 26 is played back. FIG. 7A and FIG. 7B are schematic diagrams showing an example where the display control portion 24 causes the display portion 25 to display the recorded image stored by the storage portion 26 and to display a GUI (Graphical User Interface) such as a menu screen in the rotated state. The recorded image stored by the storage portion 26 is a still image in which OSDs are superimposed on the image captured by the image pickup portion 11. Note that the recorded image is not limited to only a single image as shown in FIG. 7A and FIG. 7B, but includes a thumbnail image in which the display control portion 24 causes the display portion 25 to display a plurality of scaled-down recorded images on a single screen.

FIG. 7A is a schematic diagram of an example where the display control portion 24 causes the display portion 25 to display recorded images 701 stored by the storage portion 26 and to display a GUI 702 in the rotated state when the user is operating the endoscope apparatus 1 in the correctly directed position. As is illustrated, the user operates the endoscope apparatus 1 in the correctly directed position, and the display control portion 24 causes the display portion 25 to display the recorded images 701 stored by the storage portion 26 and to display the GUI 702 in the rotated state. In this case, the recorded images 701 and the GUI 702 look rotated at 180 degrees for the user. Therefore, there is a possibility that the use is not capable of easily checking the recorded image and the GUI.

FIG. 7B is a schematic diagram of an example where the display control portion 24 causes the display portion 25 to display the recorded images 701 stored by the storage portion 26 and to display the GUI 702 in the rotated state when the user is operating the endoscope apparatus 1 in the oppositely directed position. As is illustrated, the user operates the endoscope apparatus 1 in the oppositely directed position, and the display control portion 24 causes the display portion 25 to display the recorded images 701 stored by the storage portion 26 and to display the GUI 702 in the rotated state. In this case, the user is capable of looking at the recorded images 701 and the GUI 702 even if the user operates the endoscope apparatus 1 in the oppositely directed position. Therefore, the user is capable of easily checking the recorded image and the GUI.

When the user is operating the endoscope apparatus 1 in the correctly directed position, the display control portion 24 causes the display portion 25 to display the recorded images 701 stored by the storage portion 26 and to display the GUI 702 in the non-rotated state. In this case, the user is capable of easily checking the recorded image and the GUI. When the user is operating the endoscope apparatus 1 in the oppositely directed position as shown in FIG. 7B, the display control portion 24 causes the display portion 25 to display the recorded images 701 stored by the storage portion 26 and to display the GUI 702 in the rotated state. In this case, the user is capable of easily checking the recorded image and the GUI.

Therefore, in the present embodiment, the display control portion 24 causes the display portion 25 to display the recorded image stored by the storage portion 26 and to display the GUI in the non-rotated state in playing back the recorded image stored by the storage portion 26 in the normal mode in which user uses the endoscope apparatus 1 in the correctly directed position. Additionally, the display control portion 24 causes the display portion 25 to display the recorded image stored by the storage portion 26 and to display the GUI in the rotated state in playing back the recorded image stored by the storage portion 26 in the rotated display mode in which user uses the endoscope apparatus 1 in the oppositely directed position. In the exemplary illustration in FIG. 7, the example where the rotated display of the recorded image is combined with the rotated display of the GUI has been described above. However, the combination is not limited to this. For example, when the rotated display mode is turned on while both of the image 501 captured by the image pickup portion 11 and the GUI 702 are being displayed, the display control portion 24 may cause the display portion 25 to display the image 501 in the non-rotated state and to display the GUI 702 in the rotated state.

Next is a description of an operation of capturing an image by the endoscope apparatus 1 of the present embodiment.

Figure 8:
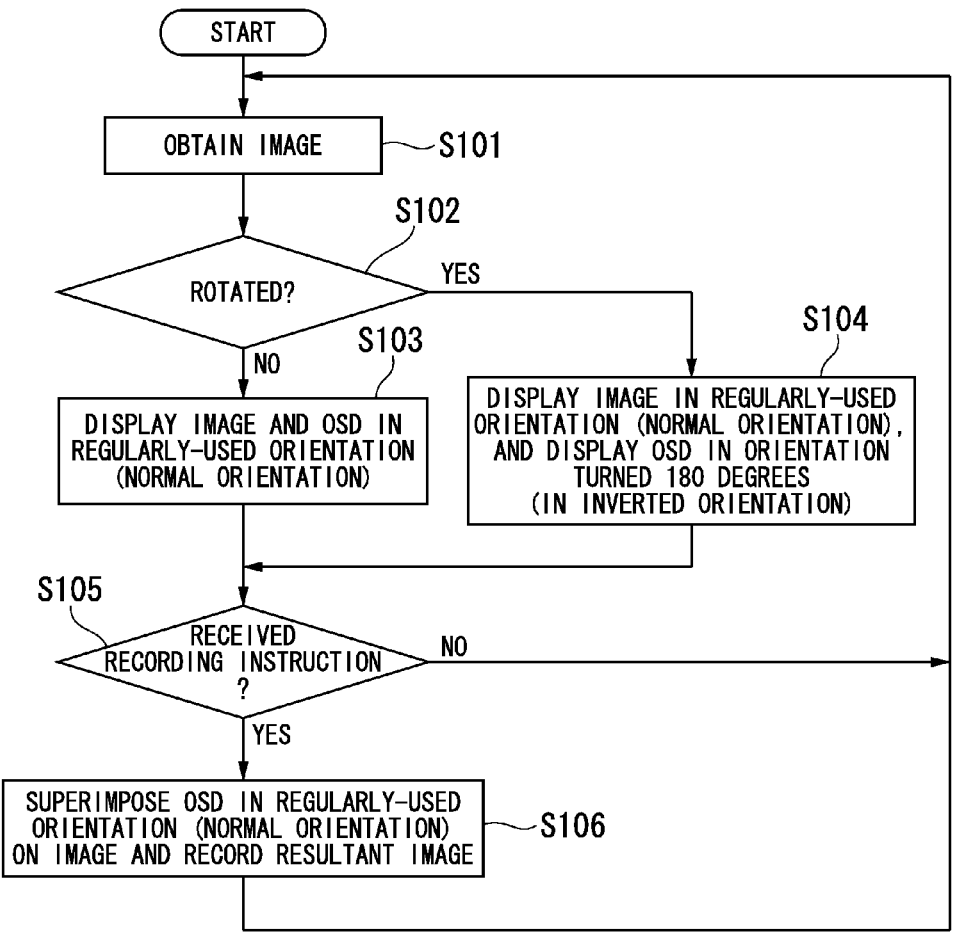
FIG. 8 is a flow chart showing an operation procedure of a capturing operation of the endoscope apparatus according to the embodiment.

FIG. 8 is a flow chart showing an operation procedure of a capturing operation of the endoscope apparatus 1. Here, the user operates a second joy stick 212 included in the operation portion 21 and sets the operation mode of the endoscope apparatus 1 in accordance with the direction in which the endoscope apparatus 1 is operated (used). The endoscope apparatus 1 sets the operation mode based on an input that the second joy stick 212 has received. To be more specific, to operate the endoscope apparatus 1 in the correctly directed position, the user sets the operation mode of the endoscope apparatus 1 to the normal mode. In addition, to operate the endoscope apparatus 1 in the oppositely directed position, the user sets the operation mode of the endoscope apparatus 1 to the rotated display mode.

(Step S101) The image pickup portion 11 captures an image. Subsequently, the image processing portion 23 performs image processing on the image captured by the image pickup portion 11. Subsequently, the display control portion 24 obtains the image on which the image processing portion 23 has performed the image processing. After that, the process moves to step S102.

(Step S102) The control portion 22 determines whether the operation mode of the endoscope apparatus 1 is the rotated display mode or not. If the control portion 22 determines that the operation mode of the endoscope apparatus 1 is the rotated display mode, the process moves to Step S104. Otherwise, the process moves to Step S103.

(Step S103) The display control portion 24 causes the display portion 25 to display the image, which has been obtained in Step S101, and to display the OSD in the non-rotated state. For example, to display the OSD in the non-rotated state, the display control portion 24 produces a non-rotated OSD and a rotated OSD, and stores them in buffer memory (not shown in the figures). The display control portion 24 then causes the display portion 25 to display the non-rotated OSD stored in the buffer memory. After that, the process moves to Step S105.

(Step S104) The display control portion 24 causes the display portion 25 to display the image, which has been obtained in Step S101, in the non-rotated state, and to display the OSD in the rotated state. For example, to display the OSD in the rotated state, the display control portion 24 causes the display portion 25 to display the rotated OSD, which has been stored in the buffer memory. After that, the process moves to Step S105.

(Step S105) If the user intends to record the image that has been captured by the image pickup portion 11 and is displayed on the display portion 25, then the user operates the second joy stick 212 included in the operation portion 21 to input a recording instruction to the endoscope apparatus 1. The control portion 22 determines whether the recording instruction has been received or not. If the control portion 22 determines that the recording instruction has been received, then the process moves to Step S106. Otherwise, the process returns to Step S101.

(Step S106) The image processing portion 23 superimposes the OSD in the non-rotated state on the image which has been subjected to the image processing in Step S101, and causes the storage portion 26 to store the resultant image as a recorded image. After that, the process returns to Step S101. As a result, the OSD in the non-rotated state is superimposed on the recorded image. Therefore, if the image is played back by a PC (Personal Computer) or the endoscope apparatus 1 in the correctly directed position, then the OSD is displayed in the non-rotated state.

Figure 9:
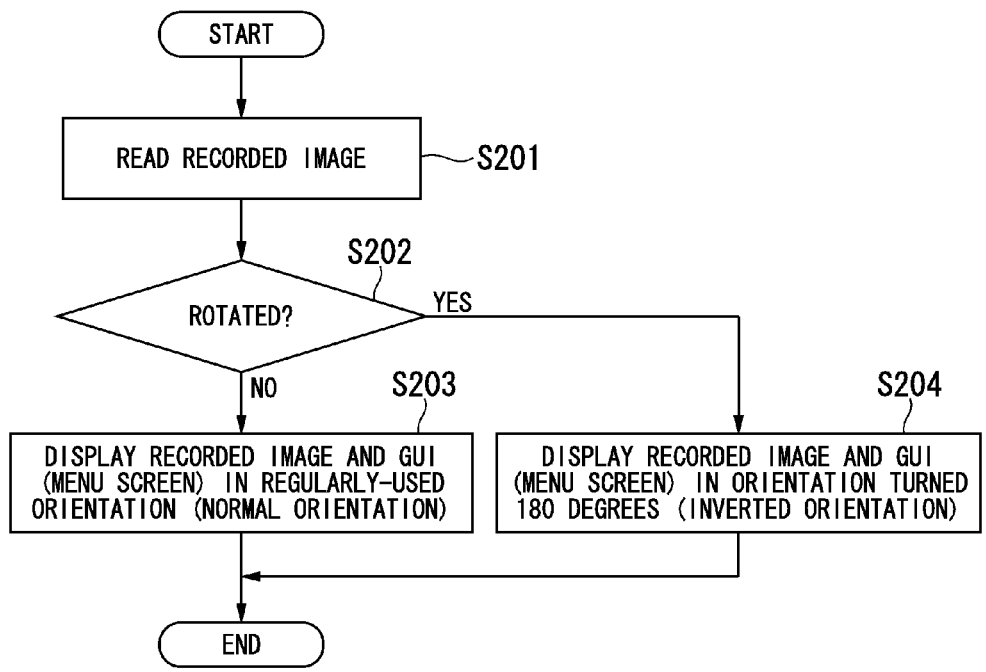
FIG. 9 is a flow chart showing an operation procedure of a playback operation of the endoscope apparatus according to the embodiment.

Next is a description of a operation of playing back a recorded image captured and stored by the endoscope apparatus 1. FIG. 9 is a flow chart showing an operation procedure of a playback operation of the endoscope apparatus 1. Similarly to when an image is captured, the user operates the second joy stick 212 included in the operation portion 21 to set the operation mode of the endoscope apparatus 1 in accordance with the position (the correctly directed position or the oppositely directed position) in which the endoscope apparatus 1 is operated (used). Based on the input received by the second joy stick 212, the endoscope apparatus 1 sets the operation mode.

(Step S201) The display control portion 24 reads a recorded image, which is an image to be played back (a playback image), from the storage portion 53. After that, the process moves to Step S202.

(Step S202) The control portion 22 determines whether the operation mode of the endoscope apparatus 1 is the rotated display mode or not. If the control portion 22 determines that the operation mode of the endoscope apparatus 1 is the rotated display mode, then the process moves to Step S204. Otherwise, the process moves to Step S203.

(Step S203) The display control portion 24 causes the display portion 25 to display the recorded image having been read in Step S201 and to display the GUI (the menu screen) in the non-rotated state.
After that, the process is terminated.

(Step S204) The display control portion 24 causes the display portion 25 to display the recorded image which has been read in Step S201 and to display the GUI (the menu screen) in the rotated state. After that, the process is terminated.

As described above, according to the present embodiment, the display control portion 24 causes the display portion 25 to display the image captured by the image pickup portion 11 and to display the OSD in the non-rotated state when an image captured by the image pickup portion 11 is displayed in the normal mode in which user uses the endoscope apparatus 1 in the correctly directed position. When an image captured by the image pickup portion 11 is displayed in the rotated display mode in which user uses the endoscope apparatus 1 in the oppositely directed position (the position in which the display portion 25 is placed upside down), the display control portion 24 causes the display portion 25 to display the image captured by the image pickup portion 11 in the non-rotated state and to display the OSD in the rotated state.

Therefore, even though an endoscope apparatus 1 in which the positional relationship between the operation portion 21 and the display portion 25 is fixed, it is possible for the user to perform operations more easily while looking at the display content on the display portion 25 when the display portion 25 is used in the oppositely directed position (the upside-down position).

Furthermore, according to the present embodiment, the display control portion 24 causes the display portion 25 to display the recorded image stored by the storage portion 26 and to display the GUI in the non-rotated state when the recorded image stored by the storage portion 26 is played back in the normal mode in which user uses the endoscope apparatus 1 in the correctly directed position. The display control portion 24 causes the display portion 25 to display the recorded image stored by the storage portion 26 and to display the GUI in the rotated state when the recorded image stored by the storage portion 26 is played back in the rotated display mode in which user uses the endoscope apparatus 1 in the oppositely directed position.

Therefore, even though the endoscope apparatus 1 in which the positional relationship between the operation portion 21 and the display portion 25 is fixed, it is possible for the user to easily check the recorded image and the GUI when the display portion 25 is used in the oppositely directed position (the upside-down position). In the present embodiment, the description has been for the case of the endoscope apparatus 1 in which the operation portion 21 and the display portion 25 are arranged in the same housing, by way of example. However, the operation portion 21 and the display portion 25 may be arranged in different housings. At this time, it is assumed that the positional relationship between the operation portion 21 and the display portion 25 is temporarily fixed due to the configuration state, or the like. Furthermore, in the present embodiment, the description has been for the case where, in the rotated display mode, the images are rotated 180 degrees, by way of example. However, the images may be rotated at every 90 degrees or the like.

Figure 10A:
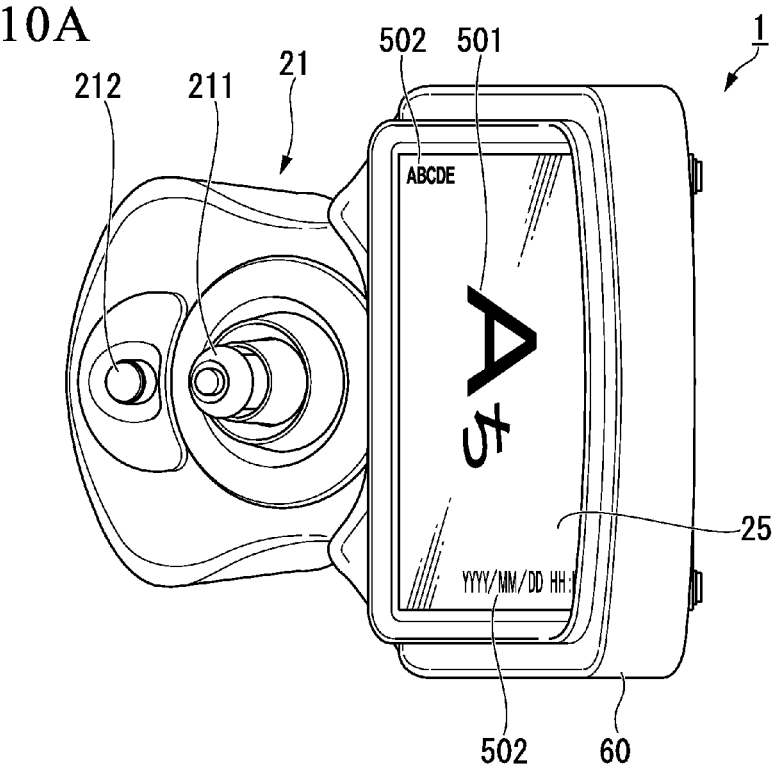
FIG. 10A is a schematic diagram showing an example where the display control portion displays, on the display portion, the image captured by the image pickup portion in the non-rotated state, and the OSDs in a left side rotated state in the embodiment.

The case where the endoscope apparatus 1 is used in a sideways position in which the endoscope apparatus 1 is rotated at approximately 90 degrees will be described below. FIG. 10A is a schematic diagram showing an example where the display control portion 24 causes the display portion 25 to display the image when the user operates the endoscope apparatus 1 being rotated at 90 degrees in the clockwise direction in FIG. 10A (a right side directed position) to an arrangement shown in FIG. 5A. In this case, the display control portion 24 causes the display portion 25 to display the image captured by the image pickup portion 11 in a non-rotated state. In addition, the display control portion 24 causes the display portion 25 to display the OSD in a state of the OSD being rotated at approximately 90 degrees in the counterclockwise direction in the display portion 25 (a left side rotated state) to an arrangement shown in FIG. 5A. As is illustrated, the user operates the endoscope apparatus 1 in the right side directed position, and the display control portion 24 causes the display portion 25 to display an image 501 captured by the image pickup portion 11 in the non-rotated state and to display an OSD 502 in the left side rotated state. In this case, the direction of the operation on the operation portion 21 by the user coincides with the direction in which the image 501 displayed on the screen moves by the bend portion 13 being bent. Furthermore, in this case, the user can read the letters on the OSD 502 even if the user operates the endoscope apparatus 1 in the right side directed position. Accordingly, the user is capable of easily performing a bending operation of the bend portion 13.

Figure 10B:
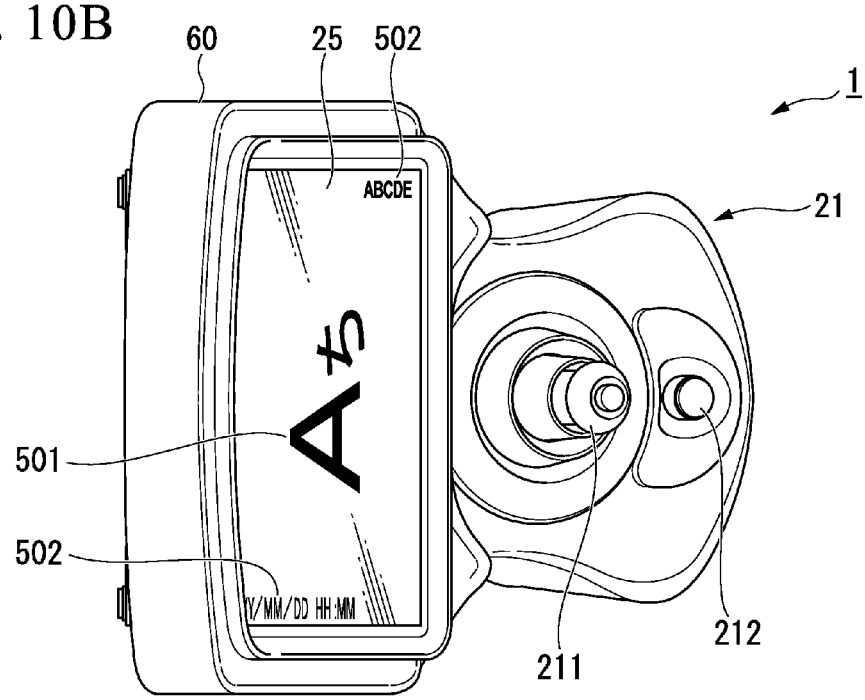
FIG. 10B is a schematic diagram showing an example where the display control portion displays, on the display portion, the image captured by the image pickup portion in the non-rotated state, and the OSDs in a right side rotated state in the embodiment.

FIG. 10B is a schematic diagram showing an example where the display control portion 24 causes the display portion 25 to display an image when the user operates the endoscope apparatus 1 being rotated at 90 degrees in the counterclockwise direction in FIG. 10B (a left side directed position) to an arrangement shown in FIG. 5A. In this case, the display control portion 24 causes the display portion 25 to display the image captured by the image pickup portion 11 in the non-rotated state. In addition, the display control portion 24 causes the display portion 25 to display an OSD being rotated at approximately 90 degrees in the clockwise direction in the display portion 25 (a right side rotated state) to an arrangement shown in FIG. 5A. As is illustrated, the user operates the endoscope apparatus 1 in the left side directed position, and the display control portion 24 causes the display portion 25 to display an image 501 captured by the image pickup portion 11 in the non-rotated state and to display an OSD 502 in the right side rotated state. In this case, the direction of the operation on the operation portion 21 by the user coincides with the direction in which the image 501 displayed on the screen moves by the bend portion 13 being bent. Furthermore, in this case, the user can read the letters on the OSD 502 even if the user operates the endoscope apparatus 1 in the left side directed position. Accordingly, since the direction of the operation on the operation portion 21 by the user is not rotated to the direction in which the image 501 displayed on the screen moves, the user is capable of easily checking the OSD 502, and is capable of easily performing an bending operation of the bend portion 13.

Therefore, in the present embodiment, the display control portion 24 causes the display portion 25 to display the image captured by the image pickup portion 11 in the non-rotated state and to display the OSD in the left side rotated state when an image captured by the image pickup portion 11 is displayed in the endoscope apparatus 1 being used in the rotated display mode in the right side directed position. Additionally, the display control portion 24 causes the display portion 25 to display the image captured by the image pickup portion 11 in the non-rotated state and to display the OSD in the right side rotated state when an image captured by the image pickup portion 11 is displayed in the endoscope apparatus 1 being used in rotated display mode in the left side directed position.

Next is a description of an example where the display control portion 24 causes the display portion 25 to display a recorded image when the recorded image that has been captured by the image pickup portion 11 and stored by the storage portion 26 is played back when the endoscope apparatus 1 is used in the sideways position.

Figure 11A:
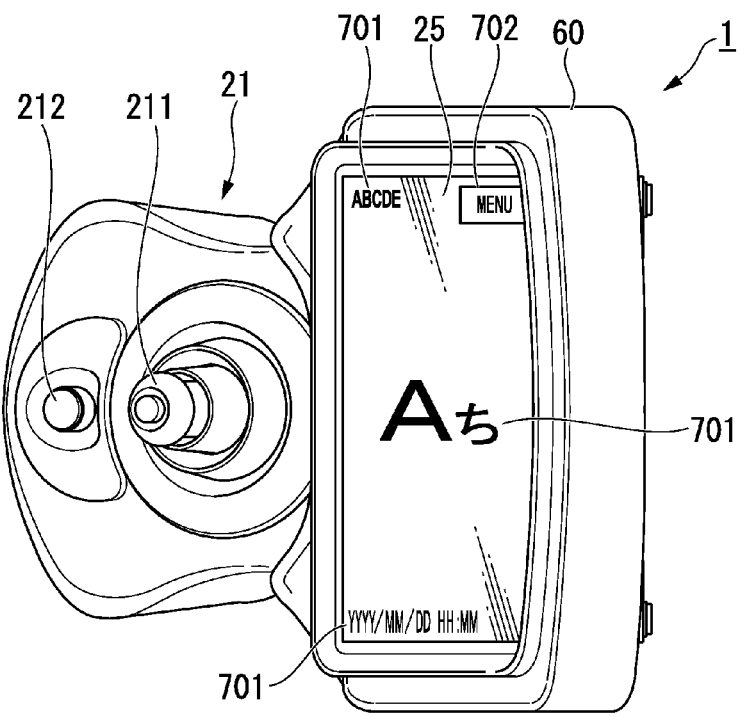
FIG. 11A is a schematic diagram showing an example where the display control portion displays, on the display portion, a recorded image stored by a storage portion and GUI such as a menu screen in a left side rotated state in the embodiment.

FIG. 11A is a schematic diagrams showing an example where the display control portion 24 causes the display portion 25 to display a recorded image 701 stored by the storage portion 26 and to display a GUI 702 in the left side rotated state when the user operates the endoscope apparatus 1 in the right side directed position. As is illustrated, when the user operates the endoscope apparatus 1 in the right side directed position and causes the display portion 25 to display the recorded image 701 stored by the storage portion 26 and to display the GUI 702 in the left side rotated state, the user is capable of looking at the recorded images 701 and the GUI 702 even if the user operates the endoscope apparatus 1 in the right side directed position. Therefore, the user is capable of easily checking the recorded image and the GUI.

Figure 11B:
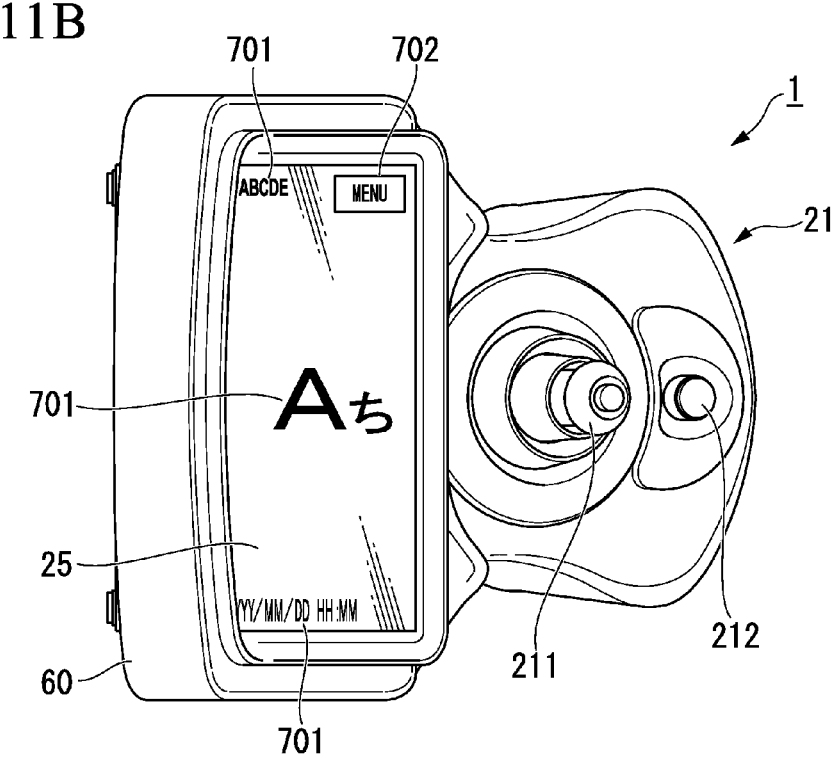
FIG. 11B is a schematic diagram showing an example where the display control portion displays, on the display portion, a recorded image stored by a storage portion and GUI such as a menu screen in a right side rotated state in the embodiment.

FIG. 11B is a schematic diagrams showing an example where the display control portion 24 causes the display portion 25 to display a recorded image 701 stored by the storage portion 26 and to display a GUI 702 in the right side rotated state when the user operates the endoscope apparatus 1 in the left side directed position. As is illustrated, the display control portion 24 causes the display portion 25 to display the recorded image 701 stored by the storage portion 26 and to display the GUI 702 in the right side rotated state when the user operates the endoscope apparatus 1 in the left side directed position. In this case, the user is capable of looking at the recorded images 701 and the GUI 702 even if the user operates the endoscope apparatus 1 in the left side directed position. Therefore, the user is capable of easily checking the recorded image and the GUI.

Next is a description of an operation of capturing an image by the endoscope apparatus 1 of the present embodiment.

In the rotated display mode in which the endoscope apparatus 1 is used in the right side directed position, the display control portion 24 causes the display portion 25 to display an image, acquired by the process in step 101 in the non-rotated state and to display the OSD in the left side rotated state in step 104. After that, the process moves to step S105. Similarly, in the rotated display mode, the display control portion 24 causes the display portion 25 to display the image, acquired by the process in step 101, in the non-rotated state and to display the OSD in the right side rotated state in step 104. After that, the process moves to step S 105. For example, as a method for displaying the OSD in the side state (the left side rotated state, the right side rotated state), the display control portion 24 causes the display portion 25 to display the OSD is rotated at 90 degrees according to a display state stored in a buffer memory.

The whole or some of the functions of the constituent elements included in the endoscope apparatus 1 may be implemented as follows. A program for implementing such functions is recorded in a computer-readable recording medium. Then, a computer system is caused to read the program recorded in the recording medium, to thereby execute the program. Note that the term "computer system" here includes an OS and hardware such as peripheral equipment.

Furthermore, the term "computer-readable recording medium" denotes a portable medium such as a flexible disk, a magneto-optical disk, a ROM, and a CD-ROM, and a storage portion such as a hard disk drive built into the computer system. Furthermore, the term "computer-readable recording medium" may include: one which dynamically retains a program for a short period of time like a communication wire when a program is transmitted via a network such as the Internet or via a communications line such as a telephone line; and one which, in the former case, retains a program for a certain period of time like a volatile memory inside the computer system serving as a server or a client. In addition, the above-mentioned program may be for implementing a part of the above-mentioned functions. Furthermore, it may be one that can implement the above-mentioned functions in combination with a program already recorded in the computer system.

While one embodiment of the present invention has been described in detail with reference to the drawings, the specific construction is not limited to that of this embodiment. Addition, omission, and replacement of the constituents, and other modifications can be made without departing from the spirit or scope of the invention. The present invention is not limited by the descriptions above, but is limited only by the appended claims.

What is claimed is:

1. An endoscope apparatus, comprising:
an insertion portion configured to include a bend portion;
an image pickup portion configured to capture an image of an object to be inspected;
an operation portion configured to perform a bending operation of the bend portion;
a storage portion configured to store at least an image of the object to be inspected as a recorded image;
a display portion configured to display the image, the display portion having a fixed positional relationship relative to the operation portion; and
a display control portion configured to:
determine a display orientation of superimposition information, the superimposition information being superimposed on the image;
display the image captured by the image pickup portion without rotating the image; and
display the superimposition information according to the display orientation of the superimposition information,
wherein the display control portion determines the display orientation of the superimposition information based on a position of the endoscope apparatus; and
wherein the display control portion does not rotate the image captured by the image pickup portion.

2. The endoscope apparatus according to claim 1, wherein the display control portion rotates the superimposition information at 180 degrees relative to the image captured by the image pickup portion when the position of the endoscope apparatus is inverted.

3. The endoscope apparatus according to claim 1, wherein the display control portion rotates the superimposition information at 90 degrees relative to the image captured by the image pickup portion when the position of the endoscope apparatus is in a right side rotated state or a left side rotated state.

4. The endoscope apparatus according to claim 1, wherein the display control portion generates non-rotated superimposition information and rotated superimposition information as the superimposition information, and the display control portion selects one of the non-rotated superimposition information and the rotated superimposition information to display the superimposition information.

5. An endoscope apparatus comprising:
an insertion portion configured to include a bend portion;
an image pickup portion configured to capture an image of an object to be inspected;
an operation portion configured to perform a bending operation of the bend portion;
a storage portion configured to store at least an image of the object to be inspected as a recorded image;
a display portion configured to display the image, the display portion having a fixed positional relationship relative to the operation portion; and
a display control portion configured to:
determine a display orientation of at least one of the recorded image and a Graphical User Interface; and
display the at least one of the recorded image and the Graphical User Interface according to the display orientation of the at least one of the recorded image and the Graphical User Interface;
wherein the display control portion determines the display orientation of the at least one of the recorded image and the Graphical User Interface based on a position of the endoscope apparatus; and
wherein the display control portion rotates both of the recorded image and the Graphical User Interface at 180 degrees when the position of the endoscope apparatus is inverted.

6. An endoscope apparatus comprising:
an insertion portion configured to include a bend portion;

an image pickup portion configured to capture an image of an object to be inspected;

an operation portion configured to perform a bending operation of the bend portion;

a storage portion configured to store at least an image of the object to be inspected as a recorded image;

a display portion configured to display the image, the display portion having a fixed positional relationship relative to the operation portion; and a display control portion configured to:
 determine a display orientation of at least one of the recorded image and a Graphical User Interface; and
 display the at least one of the recorded image and the Graphical User Interface according to the display orientation of the at least one of the recorded image and the Graphical User Interface;

wherein the display control portion determines the display orientation of the at least one of the recorded image and the Graphical User Interface based on a position of the endoscope apparatus; and wherein the display control portion rotates both of the recorded image and the Graphical User Interface at 90 degrees when the position of the endoscope apparatus is in a right side rotated state or a left side rotated state.

7. A method of displaying an image of an object to be inspected by an endoscope apparatus, the method comprising:

capturing the image using the endoscope apparatus;

displaying the image on a display portion of the endoscope apparatus;

determining a display orientation of superimposition information, the superimposition information being superimposed on the image, and the display orientation of the superimposition information being determined based on a position of the endoscope apparatus;

displaying the image without rotating the image; and displaying the superimposition information according to the display orientation of the superimposition information without rotating the displayed image;

wherein in playing back a recorded image stored in a storage portion of the endoscope apparatus, the method further comprises:
 determining a display orientation of at least one of the recorded image and a Graphical User Interface; and
 displaying the at least one of the recorded image and the Graphical User Interface according to the display orientation of the at least one of the recorded image and the Graphical User Interface.

8. The method according to claim 7, further comprising rotating the superimposition information at 180 degrees relative to the image when the position of the endoscope apparatus is inverted without rotating the image.

9. The method according to claim 7, further comprising rotating the superimposition information at 90 degrees relative to the image when the position of the endoscope apparatus is in a right side rotated state or a left side rotated state without rotating the image.

10. The method according to claim 7, further comprising generating non-rotated superimposition information and rotated superimposition information as the superimposition information, and selecting one of the non-rotated superimposition information and the rotated superimposition information to display the superimposition information.

11. The method according to claim 7, wherein determining the display orientation of the at least one of the recorded image and the Graphical User Interface comprises determining the display orientation of the at least one of the recorded image and the Graphical User Interface based on the position of the endoscope apparatus.

12. The method according to claim 11, further comprising rotating both of the recorded image and the Graphical User Interface at 180 degrees when the position of the endoscope apparatus is inverted.

13. The method according to claim 11, further comprising rotating both of the recorded image and the Graphical User Interface at 90 degrees when the position of the endoscope apparatus is in a right side rotated state or a left side rotated state.

* * * * *